United States Patent [19]

Jamison et al.

[11] Patent Number: 5,370,696
[45] Date of Patent: Dec. 6, 1994

[54] PROSTHETIC IMPLANTS WITH A HIGHLY CRYSTALLINE COATING

[75] Inventors: Russell D. Jamison, Germantown, Tenn.; Larry H. Strait, Jr., State College, Pa.; Neal B. Beals, Memphis, Tenn.; Stephen L. Van Doren, Westminster; Michael E. Marousek, Baltimore, both of Md.

[73] Assignee: Smith & Nephew Richards, Inc., Memphis, Tenn.

[21] Appl. No.: 54,716

[22] Filed: Apr. 28, 1993

Related U.S. Application Data

[63] Continuation of Ser. No. 805,875, Dec. 9, 1991, abandoned.

[51] Int. Cl.$^5$ .......................... A61F 2/28; A61F 2/30; A61F 2/02; A01N 1/02
[52] U.S. Cl. ....................... 623/16; 623/18; 623/11; 128/898
[58] Field of Search ............ 623/16, 18, 901, 11; 427/2; 128/898, 897

[56] References Cited

U.S. PATENT DOCUMENTS

| | | | |
|---|---|---|---|
| 4,126,924 | 1/1979 | Akins et al. | 427/2 X |
| 4,145,764 | 3/1979 | Suzuki et al. | 623/16 |
| 4,149,277 | 4/1979 | Bokros | 623/16 |
| 4,164,794 | 8/1979 | Spector et al. | |
| 4,351,069 | 9/1982 | Ballintyn et al. | |
| 4,356,571 | 11/1982 | Esper et al. | 623/16 |
| 4,495,664 | 1/1985 | Blanquaert | 623/18 |
| 4,662,887 | 5/1987 | Turner et al. | 623/16 |
| 4,687,487 | 8/1987 | Hintermann | 623/18 |
| 5,047,054 | 9/1991 | Vijayan et al. | 623/16 |

FOREIGN PATENT DOCUMENTS

| | | |
|---|---|---|
| 0171884 | 2/1986 | European Pat. Off. ............ 623/16 |
| 0413492 | 2/1991 | European Pat. Off. . |
| 2387028 | 11/1978 | France . |
| 2460129 | 1/1981 | France . |
| 3844290C1 | 12/1989 | Germany . |
| 55-46966 | 4/1980 | Japan . |
| 59-207233 | 11/1984 | Japan . |
| 63-303048 | 12/1988 | Japan . |
| 2128501 | 5/1984 | United Kingdom ............ 623/16 G |
| 89/10422 | 11/1989 | WIPO . |
| 89/10423 | 11/1989 | WIPO . |

OTHER PUBLICATIONS

Biederman, et al., "Plasma Deposition And Properties Of Composite Metal/Polymer And Metal/Hard Carbon Films," *Pure Appl. Chem.*, 60(5), 607–08 (1988).

Coll, et al., "Surface Modification Of Medical Implants And Surgical Devices Using TiN Layers," *Surface Coatings Technology*, vol. 36, pp. 867–878 (1988).

Herman, "Plasma-sprayed Coatings," *Scientific American*, pp. 112–117 (Sep. 1988).

Walton, "Plasma Thermal Spraying Of Stable Metal And Ceramic Coatings Over Fiber-reinforced Polymer Composite Surfaces," Int. SAMPE Tech. Conf., 20, pp. 347≧365 (1988).

*Primary Examiner*—Randall L. Green
*Assistant Examiner*—Dinh X. Nguyen
*Attorney, Agent, or Firm*—Pravel Hewitt Kimball & Krieger

[57] ABSTRACT

A coated prosthetic implant and a method of forming a continuous coating of highly crystalline polymer over a prosthetic implant by means of passing particles of polymer through a high temperature plasma and subsequently depositing the molten particles over the implant surface. This invention is especially useful for coating polymer composite implants, such as a femoral insert for a hip joint prosthesis, with a coating of poly (aryl-ether-ketone).

13 Claims, No Drawings

PROSTHETIC IMPLANTS WITH A HIGHLY CRYSTALLINE COATING

This is a continuation of co-pending application Ser. No. 07/805,875 filed on Dec. 9, 1991, now abandoned.

FIELD OF THE INVENTION

This invention relates to a method of forming a continuous coating of highly crystalline polymer over a prosthetic implant by means of passing particles of polymer through a high temperature plasma and subsequently depositing the molten particles in a substantially even distribution over the implant's surface.

This invention also relates to prosthetic implants provided with a coating of poly(ether-ether-ketone) which may be produced by the method of this invention and which acts as a barrier layer between the prosthetic implant and body fluids.

BACKGROUND OF THE INVENTION

Orthopedic implants must be strong, corrosion resistant and compatible with human tissue to provide a long useful life. Otherwise, an implant replacement operation with its attendant risks and discomfort, may be required during the lifetime of the patient. A long, useful life is most important when the recipient is young and active. To obtain useful longevity, the implant must be physically and chemically compatible with the body.

Ideally, an implant will have stiffness and elasticity identical to the healthy bone which it replaces. Many of the metal alloys, such as Ti-6A1-V4, typically used in prosthetic implants were developed for other applications, such as the aircraft industry. This alloy has an elastic modulus of about 120 GPa, far in excess of the roughly 17 GPa elasticity of healthy bone. Most other implant alloys have still higher moduli, for instance, 316 stainless steel has a modulus of about 200, and heat treated Co-Cr-Mo alloy has a modulus of about 240 GPa.

Excessive stiffness prevents the even distribution of forces along the contact surfaces between an implant and the surrounding bone. Tensile forces tend to concentrate in particular regions of the bone. In the unstressed regions of the bone, it has been found that the bone will tend to be absorbed into the body over time. This creates serious problems for the patient; notably, a weakening of the bone, a loosening of the bond between the implant and the bone, and possible shifting (i.e. sliding or rotating) of the implant relative to the bone.

Polymer composites have been tested as a possible alternative to metal alloy implants for load bearing applications such as hip joints and knee joints. For example, carbon reinforced poly(ether-ether-ketone) ("C/PEEK") and carbon reinforced triazine have been shown to have excellent stiffness and modulus for these applications.

Composite implants are presently manufactured by a process which begins with impregnating carbon fibers with the polymer. A block of composite material is built up from layers of preimpregnated carbon fiber, known as "prepregs." The block is then cut to the approximate shape of the implant. The final shape is obtained by abrading the surface with successively finer grades of sandpaper or grit. By selecting the appropriate base polymer and reinforcement, and the proper quantities of each, one can produce an implant that is "fine tuned" to its particular application. C/PEEK and carbon filled polysulfone are two such polymer composites.

Unfortunately, carbon reinforced composites like C/PEEK suffer from certain disadvantages which must be overcome before their physical properties can surpass those of metal alloys for use in load bearing implants. For instance, cutting and grinding of the composite material exposes carbon fibers at the surface of the implant. These carbon fibers are loose at the surface of the implant and are prone to fray off. These free carbon fibers may then migrate in the body of the patient or become trapped between the sliding surfaces of prosthetic joints. The abrasive action of these trapped fibers is known to cause rapid wear of the sliding surfaces.

Mechanical stresses and friction can also cause the composite lamina to separate. Delamination, as it is called, causes polymer particles and fibers to flake off and into the body where they too can become trapped between sliding surfaces of an artificial joint, or drift into body tissue.

When exposed to the in vivo environment, polymer composites are more electrochemically active than their metal alloy counterparts. Speculation has focused on the carbon reinforcement, which, it is believed, acts as an electron pathway allowing an electron exchange current to be set up between areas of the implant exposed to different ionic concentrations.

Thus, it can be seen that there are numerous difficulties that must be overcome before composites can become a favored alternative to metal alloys for use in load bearing implants.

Coating composite implants with a layer of pure polymer has been suggested as a way to overcome at least some of these difficulties. By isolating the carbon fibers underneath the surface of the implant, one is able to prevent these fibers from being trapped between sliding surfaces where they may act as an abrasive. Isolation under a nonconductive polymer coating will also prevent the carbon fibers from enhancing the electrochemical activity of the composite laminate.

Poly(ether-ether-ketone) ("PEEK") has been suggested as a coating for a C/PEEK implant. PEEK is well suited for use in an in vivo environment. It is relatively inert to corrosion or absorption in the body. Its high degree of crystallinity gives it high toughness as well as high compressive and tensile strength. Its crystallinity also makes PEEK resistant to solvation and gives it a high melting temperature. As a result of its solvation resistance, however, PEEK cannot be applied as a coating by conventional coating techniques. Only a strong acid can dissolve PEEK at room temperature. Consequently, the use of dipping or conventional spray coating would be unworkable because a solvent capable of dissolving the polymer would also tend to dissolve the implant. Furthermore, the use of solvent casting presents a problem when the workpiece is a prosthetic implant because it leaves behind volatile, potentially harmful substances which could leach into the body.

High temperature spray techniques appear to offer a promising and economical way to apply a coating of polymers, such as epoxy, polyester, polyethylene, polyamide and tetrafluoroethylene, to a metallic prosthetic implant. Kremith et. al., *Plasma Spray Application of Plastic Materials*, 12th National SAMPE Symposium, 1968, reports successful use of a plasma spraying technique to deposit such coatings on metal substrates. The investigators were able to obtain nonporous coatings at thicknesses of 0.012 to 0.015 inches, depending on the polymer. Surface adhesions were observed to be in the range of 311 to 1116 psi (much less than the 3000 psi surface adhesion achieved by use of the invention disclosed herein). The use of annealing to relieve internal stresses caused by the thermal expansion mismatch between the coating and substrate was not investigated.

Janowiecki et. al., *Plasma-Sprayed High Temperature Polymeric Coatings*, SAMPE Journal p. 40 (1968) reports the plasma spraying of polyimide and polyaryloxysilane coatings to metallic surfaces. Only a qualitative assessment of surface adhesion was made. The authors found the surface texture of their coatings generally rougher than that of low-melting polymer, applied by dip coating or conventional spray coating.

It is highly desirable to have a method of coating a polymer, polymer composite, ceramic or metal alloy implant with a highly crystalline polymer, such as PEEK, for the purpose of reducing the corrosion problems associated these implants and also to reduce the problem of wear debris formation in load bearing implant joints.

SUMMARY OF THE INVENTION

The invention provides a coated prosthetic implant fabricated of polymer, polymer composite, ceramic or metallic alloy, and a method for coating such prosthetic implants with a highly crystalline thermoplastic polymer. This method is particularly well suited for coating a prosthetic implant with a highly inert, hard coating of poly(aryl-ether-ketone), such as poly(ether-ether-ketone). Such a coating is highly desirable, in one instance, to prevent corrosion of metal and polymer composite implants by body fluids and, in another instance, to isolate the reinforcement of polymer composite materials from the in vivo environment.

Generally, the coating is made from a prepolymerized thermoplastic which has been ground into particles having an average diameter of 100μm or less. The powder is then blown through an ionized plasma and deposited onto the implant's surface. In a preferred embodiment, the implant is preheated prior to coating. After the coating has been applied, the implant is annealed to increase the crystallinity of the coating. When a coating of poly(ether-ether-ketone) is applied to a carbon filled poly(ether-ether-ketone) implant, this invention is capable of bonding the coating to the implant with surface adhesion in excess of 3000 psi.

In addition to the advantages afforded by a hard inert coating between the implant and in vivo environment, the poly(ether-ether-ketone) coating of this invention can function as a carrier for materials such as osteogenic materials, radiopaque compounds or prophylactic medication.

DETAILED DESCRIPTION OF THE PREFERRED EMBODIMENTS

The inventive method of coating a prosthetic implant with a highly crystalline polymer coating may be practiced using equipment that is well known in the art and commercially available. This equipment includes a vessel for containing the coating material (or "prepolymer") in powdered form. Preferably, the vessel is provided with a recirculation line connected to the bottom of the vessel. By pumping recirculated gas into the bottom of the vessel, it is possible to agitate and fluidize the powdered coating material, which helps maintain the powder in dry, free-flowing form. The vessel is provided with a feed line for withdrawing the powdered coating material from the vessel. A powder feed unit such as a METCO® 4MP-DUAL powder feed unit, withdraws powder from the vessel through the feed line connected to the vessel and feeds the powder to the plasma spray gun at a controlled rate.

Plasma spray guns are well known in the art and include, for example, the METCO 7MB spray gun. The spray gun is provided with a narrow nozzle, such as a METCO 3M7-GE nozzle, to impart a high spray velocity to the powder and to apply the coating in a narrow, hot band. The plasma spray gun may be equipped with one or two separate feed lines for delivery of the plasma gases. Wherein two plasma gas feed lines are provided, it is possible for the operator to adjust the temperature of the plasma by varying the feed rate of a primary and a secondary plasma gas. The gas, or gases are ignited into a plasma by an electrode connected to the plasma spray gun. A METCO 7M-63 electrode is an example of an electrode that is suitable for this purpose.

The inventive method of depositing a highly crystalline thermoplastic polymer as a coating may be used to coat a C/PEEK implant with PEEK polymer.

A pre-polymer of PEEK may be made by methods known to the prior art. It is also presently commercially available from ICI America Corp. The PEEK prepolymer is ground into particles having an average diameter of 100 μm or less. PEEK powder is highly hygroscopic and, therefore, should be kept very dry. Preferably, the powder should be dried at 100° C. or greater for 24 hrs before coating to prevent clogging of the feed lines of the plasma generating apparatus. Whether similar precautions will be required when a different polymer powder is used will depend on the nature of the polymer selected. The dried powder may be kept free flowing by fluidizing the bed with a stream of dry gas.

It may be desirable to add an additive to the coating, such as osteogenic materials, radiopaque compounds or prophylactic medication. This may be accomplished by mixing the additive in powder form with the powdered polymer or by co-extruding the additive with the polymer and then grinding the composite extrudate into particles of the appropriate size.

The powder is withdrawn from the vessel through a feed line to the plasma spray gun. The powder is delivered to the spray gun at a fixed rate by a powder feed unit. The polymer feed rate will vary depending upon polymer type and the desired thickness of the coating.

It has been discovered that temperature is an important variable in determining the texture, porosity and adhesion of the coating. It is preferable that the powder be completely melted before it contacts the surface of the prosthetic implant. Whether the powder is completely melted before contacting the implant will depend on such factors as the melting point of the polymer, the polymer feed rate, the dimensions of the spray nozzle, distance from the nozzle tip to the implant and the temperature of the plasma. When employing the method in accordance with the preferred embodiment, a 100 μm PEEK polymer powder will be completely melted and will produce a coating having maximum smoothness and minimum of porosity.

It has been found that a pure Argon plasma will maintain a suitable temperature range for practicing the invention method of coating implants. In this method, argon gas is supplied at about 75 psi pressure and at a flow rate of about 165 ml s$^{-1}$ to a plasma spray gun equipped with a very narrow spray nozzle, such as a METCO 3M7-GE nozzle. A narrow nozzle is preferred because it reduces the amount of "cold spray" onto adjacent surfaces. Cold spray refers to the sparse deposition of coating material at the edges of the spray area. This should be minimized because it tends to reduce the pull-off strength of the coating.

At the electrode of the plasma spray gun, the argon gas is ionized by an electrical arc. When a pure argon plasma is used and the electrode is a METCO 7M-63 electrode, an 800 Amp, 45–50 Volt electric current generates an electric arc that is capable of initiating the plasma.

The type of implant to which this invention can be applied is limited only by the surface properties and refractoriness of the material out of which it is constructed. When a coating of PEEK is desired, the preferred implant material is a polymer composite having a laminate construction and substantially formed of PEEK. Where a C/PEEK composite (i.e. where the polymer matrix is pure PEEK) is used, it is possible to obtain a coating having a tensile pull-off strength of 3000 psi or greater (See Table 2). This very tenacious coating can be obtained by applying the coating to a chemically untreated C/PEEK composite implant.

Before spraying, the implant should, preferably, be cleaned with an organic solvent. During spraying, the implant is cooled with air jets. The air jets are adjusted to provide an optimum substrate temperature during the spray process. Excessively high substrate temperatures can cause delamination and charring. In the preferred embodiment, wherein the implant is not chemically pretreated, it is preferred that the implant be preheated immediately prior to spraying sufficient to bring the surface temperature of the implant as close to the melting point of the polymer matrix (343° C. for PEEK) as possible without distorting or degrading the substrate. Preheating can be accomplished conveniently by a pass of the spray gun with the powder flow shut off, immediately prior to applying the coating. It is further preferred that the spray area be post-heated by a pass of the spray gun (with powder flow shut off) immediately after the coating is applied.

A highly tenacious coating is obtained when the substrate is sprayed in accord with the following preferred procedure. The substrate surface is preheated with one pass of the spray gun with the powder flow shut off. Immediately thereafter, the coating is applied by two passes of the spray gun. Immediately after the spraying passes, another post-heating pass is made with the powder flow shut off. These steps (one preheating pass, followed by two spraying passes, followed in turn by one post-heating pass) constitute an "iteration." The entire surface of the substrate is coated by repeating the iteration and stepping, or offsetting, the gun with each iteration in the direction perpendicular to the direction of travel during a pass.

For coating a 1½×1½ inch coupon, the preferred parameters of the process further include a spray nozzle to substrate distance of 3 inches and a traverse rate of roughly 600 mm s$^{-1}$. When a step increment of 3.175 mm is used to spray 1½×1½ inch coupons, a 0.010 inch to 0.015 inch coating is obtained at a polymer feed rate of 20 g min$^{-1}$. The thickness of the final coating can be varied by adjusting such parameters as the step increment, polymer feed rate, the traverse rate and the diameter of the spray nozzle. Coating an area of larger size will also require routine adjustment of these spray parameters.

While it is preferred to use a chemically untreated implant in conjunction with preheating and postheating the implant, an alternative embodiment of this invention yields a coating with good tenacity without the need for preheating or postheating the implant (See Example 1b, Samples 6 through 9). In this alternative embodiment, the implant is chemically treated prior to coating.

Exposing the substrate to fluorine gas prior to spraying results in improved tensile pull-off strength relative to a chemically and thermally untreated substrate. Generally, greater improvement in bonding between the substrate and coating results as the level exposure is increased, both in terms of fluorine concentration and exposure time.

In the thermally pretreated, preferred embodiment and the chemically pretreated, alternative embodiment, the implant is annealed after applying the coating to reduce residual stresses in the coating and to improve the crystallinity of the coating. Higher crystallinity is desirable or the PEEK barrier coating because the crystalline phase has a higher density and lower free volume. It is therefore less permeable to solvents. However, where mechanical properties (strength, toughness, fatigue endurance), solvent resistance and wear resistance are not critical to the application, annealing may be dispensed with as it has little effect on surface adhesion between the coating and the implant.

Annealing may be commenced immediately after the implant has been coated. The optimum temperature profile and duration of the annealing process for a particular application may be determined by routine experimentation and will depend on the composition of the implant, the coating selected, and the coating thickness. When a coating of PEEK having a thickness in the range of 0.010 inches to 0.015 inches is applied to a C/PEEK implant, it is preferred to anneal the implant for about 4½ hours. According to the preferred temperature profile, the temperature is linearly increased from ambient to 200 ° C. over a period of 2 hours and maintained at 200 ° C. for half an hour, followed by a linear decrease in temperature back to ambient temperature.

Using the process of this invention, it is possible to obtain a PEEK coating over a C/PEEK implant having a surface adhesion of 3000 psi or greater (see Example 1b, Samples 5 through 9). The resultant coating has a moderate degree of porosity, with little interconnectivity between pores. Therefore, this coating can provide an effective barrier between the in vivo environment and an orthopedic implant. The PEEK coating produced by the preferred method of this invention is black in color and has a moderately textured surface finish.

EXAMPLES

Materials and Equipment

The poly(ether-ether-ketone) powder used to make the coating was Victrex PEEK Grade 150PF powder, having a particle diameter range from 10–100µm. The powder was dried at about 120° C. for about 24 hrs before use to obtain a smooth flow rate to the plasma sprayer. Powder was delivered to the plasma spray nozzle by a METCO 4MP-DUAL power feed unit at a rate of about 20 g min$^{-1}$. A METCO 7MB plasma spray gun was used to vaporize and melt the polymer. The spray gun was equipped with a METCO 3M7-GE nozzle and METCO 7M-63 Electrode. The plasma gas used was Argon, supplied at 75 psi pressure and a flow rate of 165 ml min$^{-1}$. A hydrogen backpressure of 50 psi was maintained with a zero hydrogen flow rate. The plasma was generated by an 800 amp, 45-50 volt current passing through the METCO 7M-63 electrode.

The spray gun traversed the coupons at a rate of 600 mm s$^1$ and an offset of 3.175 mm per sweep. Before coating, the spray gun was passed once over the coupons to raise the surface temperature. A thermocouple embedded 0.008 inches below the surface of the coupons measured a rapid increase in near subsurface temperature during the pass, which decayed to a steady 80° C. between the preheat and spray passes.

The coating was then applied by two passes of the spray gun over the coupons. The coupons were then post-heated with another pass of the spray gun. During pre-heating, spraying and post-heating, the coupons were cooled by two air jets (110 psig), one mounted parallel to the front surface of the coupons and the other perpendicular to the back surface of the coupons.

After the coating was applied, the coupons were annealed for a period of about 4½ hrs, holding a maximum temperature of 200° C. for 30 minutes.

Pull-off adhesion tests were conducted using a SEMicro ® PATTI-2A pneumatic adhesion tensile strength testing apparatus, modified to prevent flexing of the coupons during testing. The adhesive used for bonding the pull-stubs to the coating was 3M ®Scotch-Weld 1838 B/A epoxy, having a tensile strength of 4000 psi. One half inch diameter pull-stubs were used. These were prepared by grit-blasting and immersion in an ultrasonic acetone bath to insure a strong bond to the adhesive. The pull-stubs were bonded to the coated surface of the coupons and allowed to cure in a desiccator at room temperature for 24 hrs.

Example 1a (variation in substrate temp. and spray distance)

In Example 1a, 1½×1½×⅛ inch coupons of C/PEEK were used for the substrate. The coupons were composed of BASF AS4/PEEK powder prepreg in a [0/90]$_{6S}$ layup. Approximately 0.001" of material was machined off of the surface to be coated and then wet-sanded using 320 grit sandpaper to simulate the machined surface of a C/PEEK prosthetic implant. Thirty, 1½×1½×⅛ inch coupons were sprayed at various power settings, traverse rates, spray distances and step increments. Some of the coupons were sprayed with an unmodified plasma spray gun as previously described. Others were sprayed with a gun having two high velocity air jets adjacent to the spray nozzle to further cool the coupons during spraying. Note, these air jets were in addition to the immobile air jets used to cool the coupons.

Each coupon was visually examined by microscope and the coupons having the smoothest surface finish were selected for tensile pull-off testing. The results of these tests are reported in Table 1.

TABLE 1

| Sample | Spray distance (in.) | High Velocity Air Jets | Tensile Bond Strength (psi) |
|---|---|---|---|
| 1 | 3.5 | No | 926 ± 6 |
| 2 | 3.0 | No | 1511 ± 245 |
| 3 | 3.0 | Yes | 493 ± 43 |
| 4 | 3.5 | Yes | 366 ± 65 |

A comparison of results indicates that cooling the coupons with air jets mounted on the plasma spray gun causes poorer surface adhesion. Further, it was found that surface adhesion decreases significantly when the spray distance is greater than 3 inches.

Example 1b (effect of pre-heating and surface treatment)

In Example 1b, the same substrate material was used as in Example 1a. However, ½ inch thick coupons were used to determine the effect that flexing of the coupons during pull-off testing might have on the measured surface adhesion. The 1½×1½×1½ inch C/PEEK coupons were also used to test the effect of surface treating the coupons. Two coupons were prepared according to each treatment. One coupon was then coated without a preheating pass of the spray gun and the other coupon was preheated immediately prior to spraying so that the effect of surface preheating could be further characterized. Three pull-tests were made from each coupon and their results were averaged and are reported in Table 2.

TABLE 2

| Sample | [F$_2$] | Exposure Time | Tensile Strength without preheat (psi) | Tensile Strength with preheat (psi) | Percent Change |
|---|---|---|---|---|---|
| 5 | — | — | 2204 ± 391 | 3345 ± 469 | +52 |
| 6 | high | long | 2775 ± 124 | 3087 ± 70 | +11 |
| 7 | low | long | 2829 ± 154 | 3195 ± 432 | +13 |
| 8 | high | short | 2761 ± 401 | 3433 ± 202 | +24 |
| 9 | low | short | 2041 ± 154 | 3521 ± 94 | +73 |

The results of Samples 6 and 7 show that surface treating the substrate with reactive gas having a high fluorine concentration for relatively long exposure times significantly improves adhesion when the substrate is not pre-heated. Further, a comparison of Sample 5 with Samples 6 through 9 shows that surface treatment has no statistically significant effect when the substrate is preheated.

A comparison of Sample 2 with Sample 5 indicates a large increase in tensile strength when a thicker (½ inch v. ⅛ inch) coupon is used. Poorer pull-test results for the ⅛ inch coupons are likely due to flexing of the coupon during the pull-test. As a result of bending, shear forces built up within the coupon and at the coating/substrate interface and contributed to bond failure between the coating and the coupon.

Although the invention has been described with reference to its preferred embodiments, those of ordinary skill in the art may, upon reading this disclosure, appreciate changes and modifications which may be made and which do not depart from the scope and spirit of the invention as described above and claimed hereafter.

We claim:

1. A method of applying a coating of highly crystalline polymer to a prosthetic implant comprising:
    passing a powder of polyaryletherketone through a plasma of ionized gas to at least partially melt the powder and;
    depositing the at least partially molten powder onto at least a portion of the surface of a prosthetic implant to form a tenacious coating substantially free of interconnecting porosity on said surface.

2. The method of claim 1 further comprising annealing the coated implant.

3. The method of claim 2, wherein the coating has a thickness from about 0.005 to about 0.015 inches and a tensile pull-off strength of greater than about 2500 psig.

4. The method of claim 1 wherein the pull-off strength of the coating exceeds about 2500 psig.

5. The method of claim 1 wherein particles of polyaryletherketone powder have an average diameter of about 200 μm or less.

6. The method of claim 1, wherein the coating has a thickness from about 0.005 to about 0.015 inches and a tensile pull-off strength of greater than about 2500 psig.

7. A prosthetic implant having a polyaryletherketone coating applied by a process comprising:
 passing a powder of polyaryletherketone through a plasma of ionized gas to at least partially melt the powder and;
 depositing the at least partially molten powder onto at least a portion of a surface of a prosthetic implant to form a tenacious coating thereon substantially free of interconnecting porosity.

8. The prosthetic implant of claim 7 wherein the prosthetic implant comprises a fiber reinforced polymer composite.

9. The prosthetic implant of claim 7 wherein the prosthetic implant comprises a fiber reinforcement embedded in a polymer matrix, wherein the polymer is selected from the group consisting of poly(aryl-ether-ketones), polysulfone, triazine and mixtures thereof.

10. The method of claim 1 wherein the prosthetic implant comprises a fiber reinforced polymer composite.

11. The method of claim 10, wherein the composite includes a matrix selected from the group consisting of poly(aryl-ether-ketones), polysulfone, triazine, and mixtures thereof.

12. The prosthetic implant of claim 7, wherein the coating has a thickness from about 0.005 to about 0.015 inches and a tensile pull-off strength of greater than about 2500 psig.

13. A prosthetic implant having a polyaryletherketone coating applied by a process comprising:
 passing powdered polyaryletherketone, having a particle size less than about 200 microns, through a plasma of ionized gas to at least partially melt the powdered polyaryletherketone;
 depositing the at least partially molten polyaryletherketone onto at least a portion of a surface of a prosthetic implant to form a coating thereon substantially free of interconnecting porosity, said coating having a thickness ranging from about 0.005 to about 0.015 inches, said coating adhering to said surface with a pull off strength greater than about 2500 psig.

* * * * *